(12) United States Patent
Vrane et al.

(10) Patent No.: US 9,092,034 B2
(45) Date of Patent: Jul. 28, 2015

(54) DUAL FEEDBACK VACUUM FLUIDICS FOR A FLOW-TYPE PARTICLE ANALYZER

(71) Applicant: Becton, Dickinson and Company, Franklin Lakes, NJ (US)

(72) Inventors: David Vrane, San Jose, CA (US); Pierce O. Norton, Morgan Hill, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 212 days.

(21) Appl. No.: 13/960,681

(22) Filed: Aug. 6, 2013

(65) Prior Publication Data

US 2014/0158212 A1    Jun. 12, 2014

Related U.S. Application Data

(63) Continuation of application No. 13/239,256, filed on Sep. 21, 2011, now Pat. No. 8,528,427.

(60) Provisional application No. 61/407,990, filed on Oct. 29, 2010.

(51) Int. Cl.
| | |
|---|---|
| *G01N 15/10* | (2006.01) |
| *G01N 35/08* | (2006.01) |
| *G05D 16/00* | (2006.01) |
| *G01N 15/14* | (2006.01) |

(52) U.S. Cl.
CPC ............ *G05D 16/00* (2013.01); *G01N 15/1404* (2013.01); *G01N 2015/1409* (2013.01); *Y10T 137/0379* (2015.04)

(58) Field of Classification Search
CPC .................... G01N 15/1404; G01N 2015/149; G01N 15/14; G01N 15/1434; G01N 2015/1006; G01N 2015/1409; G01N 2015/1486; G01N 21/05; G01N 21/1702; G01N 21/3563; G01N 21/64; G01N 35/1095
See application file for complete search history.

(56) References Cited

U.S. PATENT DOCUMENTS

| | | |
|---|---|---|
| 5,395,588 A | 3/1995 | North, Jr. et al. |
| 5,915,925 A | 6/1999 | North, Jr. |
| 6,382,228 B1 | 5/2002 | Cabuz et al. |

(Continued)

FOREIGN PATENT DOCUMENTS

| | | |
|---|---|---|
| GB | 2381589 A | 5/2003 |
| WO | WO 03/032101 A1 | 4/2003 |

*Primary Examiner* — David A Rogers
(74) *Attorney, Agent, or Firm* — Bret E. Field; Bozicevic, Field & Francis LLP

(57) ABSTRACT

The present invention relates to a vacuum-driven fluidic system for a flow-type particle analyzer. The system includes a vacuum pump which creates a pressure drop downstream of the flow cell, which pulls sheath fluid and sample fluid through the flow cell. A variable-resistance fluidic resistor is configured to control the ratio of sample fluid flow to sheath fluid flow. Dual feedback circuits, one configured to modulate the vacuum pump power in response to the pressure drop across the flow cell, referred to as the dynamic pressure drop, and a second configured to modulate the vacuum pump power in response to the pressure drop created by the vacuum pump relative to ambient pressure, referred to as the static pressure drop, are used to automatically control the system. The present invention enables adjustment of the sample fluid flow rate while maintaining a constant total fluid flow through the flow cell, and further, enables pausing the system without significant fluctuations in the vacuum.

11 Claims, 6 Drawing Sheets

(56) References Cited

U.S. PATENT DOCUMENTS

| | | |
|---|---|---|
| 6,694,799 B2 | 2/2004 | Small et al. |
| 6,825,926 B2 | 11/2004 | Turner et al. |
| 7,381,565 B2 | 6/2008 | Kurabayashi et al. |
| 7,997,831 B2 | 8/2011 | Gilbert et al. |
| 8,017,402 B2 | 9/2011 | Rich et al. |
| 8,187,888 B2 | 5/2012 | Rich et al. |
| 8,262,990 B2 | 9/2012 | Blair et al. |
| 8,283,177 B2 | 10/2012 | Ball et al. |
| 8,303,894 B2 | 11/2012 | Rich et al. |
| 8,445,286 B2 | 5/2013 | Blair et al. |
| 8,470,246 B2 | 6/2013 | Rich et al. |
| 8,507,279 B2 * | 8/2013 | Ball et al. ............... 436/10 |
| 8,715,573 B2 * | 5/2014 | Ball et al. ............... 422/81 |
| 2002/0028434 A1 | 3/2002 | Goix et al. |
| 2003/0054558 A1 | 3/2003 | Kurabayashi et al. |
| 2003/0062314 A1 | 4/2003 | Davidson et al. |
| 2003/0129090 A1 | 7/2003 | Farrell et al. |
| 2003/0138967 A1 | 7/2003 | Hall et al. |
| 2003/0211009 A1 * | 11/2003 | Buchanan ............... 422/63 |
| 2005/0073686 A1 | 4/2005 | Roth et al. |
| 2005/0105077 A1 | 5/2005 | Padmanabhan et al. |
| 2006/0078998 A1 | 4/2006 | Puskas et al. |
| 2007/0125436 A1 | 6/2007 | Rich et al. |
| 2007/0212262 A1 | 9/2007 | Rich et al. |
| 2008/0108146 A1 | 5/2008 | Jiang et al. |
| 2008/0218753 A1 | 9/2008 | Chang et al. |
| 2009/0104075 A1 | 4/2009 | Rich |
| 2011/0061471 A1 | 3/2011 | Rich et al. |
| 2012/0056086 A1 | 3/2012 | Bandura et al. |
| 2012/0070818 A1 | 3/2012 | Rowlen et al. |
| 2012/0122084 A1 | 5/2012 | Wagner et al. |

* cited by examiner

DUAL FEEDBACK VACUUM FLUIDICS FOR A FLOW-TYPE PARTICLE ANALYZER

BACKGROUND OF THE INVENTION

1. Field of the Invention

The present invention relates to instruments for the analysis of particles in a fluid, and their use.

2. Description of Related Art

Flow-type particle analyzers, such as flow cytometers, are well known analytical tools that enable the characterization of particles on the basis of optical parameters such as light scatter and fluorescence, or by electrical properties, such a impedance. In a flow cytometer, for example, particles, such as molecules, analyte-bound beads, or individual cells, in a fluid suspension are passed by a detection region in which the particles are exposed to an excitation light, typically from one or more lasers, and the light scattering and fluorescence properties of the particles are measured. Particles or components thereof typically are labeled with fluorescent dyes to facilitate detection, and a multiplicity of different particles or components may be simultaneously detected by using spectrally distinct fluorescent dyes to label the different particles or components. Typically, detection is carried out using a multiplicity of photodetectors, one for each distinct dye to be detected. Both flow and scanning cytometers are commercially available from, for example, BD Biosciences (San Jose, Calif.). A description of flow cytometers is provided in Shapiro, 2003, Practical Flow Cytometry, 4th ed. (John Wiley and Sons, Inc. Hoboken, N.J.), and in the references cited therein, all incorporated herein by reference.

In a typical flow cytometer, the particle-containing sample fluid is surrounded by a particle-free sheath fluid that forms an annular flow coaxial with the sample fluid as is passes through the detection region, thereby creating a hydrodynamically focused flow of particle-containing sample fluid in the center of the fluid stream, surrounded by particle-free sheath fluid. Typically, the ratio of sheath fluid to sample fluid is high, with the sample fluid forming only a small fraction of the total fluid flow through the detection region.

Typically, flow cytometer systems have been implemented using pressure-driven fluidics in which the sample and sheath fluid are provided to a flow cell, which contains the detection region, under a pressure greater than ambient pressure. Changes in the flow rate through the flow cell of a pressure-driven fluidics system are achieved by varying the pressure in the sample tube and/or the sheath fluid reservoir that feed into the flow cell. The ratio of sample fluid to sheath fluid flowing through the flow cell is governed both by the pressure levels in the sample tube and sheath fluid reservoir, and by the ratio of the resistances of the sample fluid and sheath fluid paths.

Alternatively, flow cytometer systems have been implemented using vacuum-driven fluidics in which a vacuum pump draws a vacuum downstream of the flow cell, and the sample and sheath fluids are held at ambient pressure. Changes in the flow rate through the flow cell of a vacuum-driven fluidics system are achieved by varying the vacuum drawn by the vacuum pump, and the ratio of sample fluid to sheath fluid flowing through the flow cell is governed by the ratio of the resistances of sample fluid and sheath fluid paths.

In general, the design of pressure-driven fluidics systems is more complicated than is the design of vacuum-driven fluidics systems because of the need for components, including tubing, connections, and seals, that withstand high system pressure levels. In contrast, in a vacuum-driven flow cytometry system, the design of the fluidic connections to the sample tube and sheath fluid supply reservoir is greatly simplified as it does not require the use of pressurizable tubings, connections, and seals. The elimination of pressurized sample tubes further facilitates the design of auxiliary equipment, such as automatic tube lifters and robotic sample loaders.

U.S. Pat. No. 5,395,588, incorporated herein by reference, describes a vacuum control system for use in a flow cytometer. The system includes a vacuum pump that pulls a sheath fluid from an open supply reservoir through a flow cell wherein cell analysis occurs, and discharges the flow cell effluent to an open waste reservoir. A pressure drop is created through the conduit leading from the supply reservoir to the flow cell, which also aspirates a sample consisting of a particle (e.g., cell) suspension from an open sample vessel into and through the flow cell. The flow rate of the system is regulated by monitoring the vacuum level at the outlet of the flow cell. A control circuit coupled to the vacuum sensor adjusts the electric power applied to the vacuum pump motor to maintain a predetermined vacuum level at the outlet of the flow cell.

BRIEF SUMMARY OF THE INVENTION

The present invention provides an improved vacuum-driven fluidics system for a flow-type particle analyzer in which two or more fluidic sources, such a sample fluid and a sheath fluid, are combined by the system just prior to analysis, such as in a flow cytometer.

The vacuum-driven fluidics system of the present invention, as used in a flow cytometer, includes a vacuum pump that develops a vacuum that draws sheath fluid from a sheath reservoir and sample fluid containing the particles to be analyzed from a sample tube through a flow cell, wherein analysis of the particles is carried out. Waste effluent, which is the mixture of sample and sheath fluids exiting the flow cell, is drawn through the pump and discharged into a waste reservoir. A pressure sensor (pressure transducer) is configured to measure the pressure drop across the flow cell, referred to herein as the dynamic pressure drop. A first control feedback circuit, referred to herein as the dynamic control feedback circuit, is provided that enables regulating the dynamic pressure drop by modulating the vacuum pump in response to the measured dynamic pressure drop.

In preferred embodiments, the vacuum-driven fluidics system further includes a second pressure sensor (pressure transducer) configured to measure the vacuum relative to the ambient pressure drawn by the vacuum pump, referred to herein as the static pressure drop. A second control feedback circuit, referred to herein as the static control feedback circuit, is provided that enables regulating the static pressure drop by modulating the vacuum pump motor in response to the measured static pressure drop. The control circuits allow selection of either the first, dynamic, or the second, static, control feedback circuit, such that the vacuum pump motor may be modulated in response to either the dynamic pressure drop or the static pressure drop. The function of the two feedback control circuits is described further below.

Preferably, the vacuum pump is modulated to control the amount of vacuum drawn by the pump by modulating the electrical power provided to the pump motor. Alternatively, the vacuum pump can be modulated to control the amount of vacuum drawn using one or more adjustable valves or other fluidic resistors that restrict the flow of fluid through the pump.

In preferred embodiments, the vacuum-driven fluidics system of the present invention further includes a variable-resistance fluidic resistor in the sheath fluid path positioned between the sheath fluid reservoir and the flow cell. By varying the resistance of the variable-resistance fluidic resistor, the relative proportion of sheath fluid and sample fluid drawn through the flow cell can be modulated. Equivalently, the sample fluid flow rate can be modulated by changing the resistance of the sheath fluid path while maintaining a constant total flow rate through the flow cell.

Alternatively, the vacuum-driven fluidics system of the present invention further includes a variable-resistance fluidic resistor in the sample fluid path positioned between the sample fluid tube and the flow cell. The variable-resistance fluidic resistor in the sample fluid path also may be used in conjunction with a variable-resistance fluidic resistor in the sheath fluid path. In general, it is preferable to control the ratio of sample to sheath fluid using a variable-resistance fluidic resistor in the sheath fluid path. In a typical flow cytometer, the flow of sheath fluid is on the order of 1,000 times the flow of sample fluid (typical sheath fluid flow is on the order of milliliters per minute; typical sample fluid flow is on the order of microliters per minute), and it is easier to control the flow of sheath fluid with precision.

An advantage of the vacuum-driven fluidics system of the present invention is that the sample fluid flow rate can be modulated while maintaining a constant total flow rate through the flow cell. The total flow rate is held constant using the first (dynamic) feedback control loop, modulating the power of the vacuum pump to provide a constant dynamic pressure drop, as measured by first pressure sensor. In contrast, previously described flow cytometers using vacuum-driven fluidics, such as those described in U.S. Pat. No. 5,395,588, only measured and controlled the static pressure drop. A constant static pressure drop provides a constant flow rate through the cuvette only if the fluidic resistances of the sample and sheath paths upstream of the flow cell are constant. A change in the sample flow rate in a vacuum-driven fluidic system that monitors only the static pressure drop would require extensive recalibration of the required static pressure drop.

In some embodiments of the invention, the variable-resistance fluidic resistor is configured to provide a plurality of discrete resistance levels. Preferably, this is achieved by providing alternative selectable fluid paths, each fluidic path having a different fluidic resistance. The fluid paths may be a conduits (e.g., lengths of tubing) having different lengths or diameters. Valves are situated in the sheath fluid path to allow selection of a desired fluid path from among the plurality of alternative fluid paths.

In alternative embodiments of the invention, the variable-resistance fluidic resistor is continuously variable. In preferred embodiments, the sheath fluid path includes a conduit composed of an at least partially compressible or deformable material, such as length of plastic tubing, and an adjustable pressure is applied to the outside of the tubing. Modulation of the pressure applied to the outside of the tubing changes alters the diameter and/or shape of the tubing, thereby changing the cross-sectional area of the fluidic path and, concomitantly, changing the fluidic resistance of the tubing.

The continuously variable variable-resistance fluidic resistor may consist of a length of tubing that is compressed mechanically. For example, the tubing may be wound around a cylindrical post and compressed between plates, at least one movable, having surfaces perpendicular to the post. Alternatively, the continuously variable variable-resistance fluidic resistor may consist of a length of tubing that passes through the interior of a pressure chamber having an adjustable internal pressure. The internal pressure of the pressure chamber may be modulated by connecting the chamber to adjustable pressure source, such as a compressed air source, or by altering the size and/or shape of the pressure chamber, such as by mechanical means.

The modulation of the resistance of the variable-resistance fluidic resistor can be put under automated control using servomechanisms to effect changes in the resistance settings.

The flow of sample and sheath through the system can be paused to allow, for example, a change to a new sample source after each sample analysis. In the present system, the flow of fluid may be paused by closing a valve situated in the fluid path between the flow cell and the pump. When this valve is closed, the dynamic pressure drop drops to zero, the dynamic feedback loop, which is between the dynamic pressure drop and the pump, is stopped, and the static feedback loop, which is between the static pressure drop and the pump, is activated. The static feedback loop enables maintaining the static pressure drop at a constant level during the paused state, preferably maintaining it at the static pressure drop of the system that existed while in the running state prior to pausing the system (while under control of dynamic feedback loop). When the flow of fluid through the flow cell is restarted, control of the pump is switched back to the dynamic feedback loop, which enables re-establishing and maintaining the flow across the flow cell at the same rate as it was prior to pausing the system, regardless of any changes made to the resistance level of the variable-resistance fluidic resistor while the system was paused. This switching between feedback control circuits eliminates large fluctuations in the vacuum during transitions between running and paused states, while maintaining a constant flow rate through the flow cell for all samples.

A constant flow rate through the flow cell, or more specifically, through the cuvette within a the flow in which cell analysis takes place, is particularly important in a multi-laser flow cytometer. A multi-laser flow cytometer typically has multiple spatially separated detection regions which the particles pass through as they flow through the cuvette. In order to match up the signals detected in each of the detection regions such that all signals from the same particle can be identified as coming from the particle, the transit time from one detection region to the next must be determined. Typically, using a two laser system, the signals measured after excitation with the first laser in the first detection region are held in an electronic circuit until the signals measured after excitation with the second laser in the second detection region have been measured, and the two signals are then sent together for further analysis. The time between arrival of the first signal and arrival of the second signal, often referred to as a "laser delay", depends on the distance between the detection regions and on the flow rate. Similarly, in multi-laser system having more that two lasers, each of the signals from the same particle are stored until the last signal is measured, and the multiple signals are then passed on to the downstream electronics for further analysis. The vacuum-driven fluidic system of the present invention enables maintaining a constant flow rate through the cuvette, which insures constant laser delays, while allowing the sample flow rate to be altered.

DETAILED DESCRIPTION OF THE INVENTION

Figure 1:
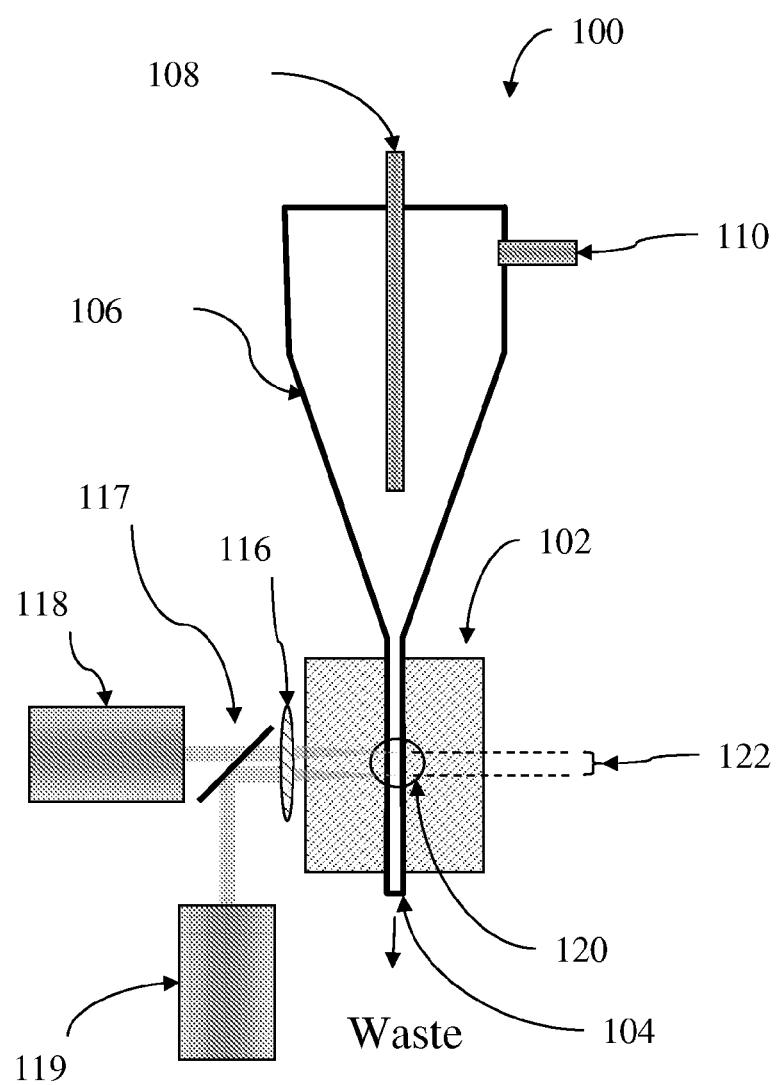
FIG. 1 provides a schematic representation of elements of a flow cell from a typical flow cytometer. The direction of fluid flow in FIG. 1 is from the top of the page towards the bottom.

The following definitions are provided for clarity. Unless otherwise indicated, all terms are used as is common in the art. All reference cited herein, both supra and infra, are incorporated herein by reference.

A "flow-type particle analyzer" is used herein to refers to any instrument that analyzes particles suspended in a flowing fluid stream by passing the particles past one or more optical detectors, and includes, for example, analyzing or sorting flow cytometers, hematology analyzers, and cell counters. A flow-type particle analyzer contains at least two fluid sources, and the two fluid are combined by the system just prior to analysis. For example, a flow cytometer of the present invention analyzes particles suspended in a sample fluid that is hydrodynamically focused by a sheath fluid.

Sheath fluid refers to a substantially particle-free fluid that is used to surround the particle-containing sample fluid to achieve hydrodynamic focusing, as commonly practiced in a flow cytometer.

The terms "pressure sensor", "pressure transducer", "vacuum sensor", "vacuum transducer", and "transducer", with reference to measuring pressure, are all used interchangeably herein.

A fluidic "line", as used herein, refers to a fluid conduit or channel for transporting fluid. Typically, the sample fluid line and sheath fluid line will consist primarily of lengths of tubing, although the lines may include valves and additional fluidic resistors.

Pressure Transducers

A typical pressure sensor incorporates a diaphragm of a piezoresistive material which generates a proportional voltage when deflected in response to a pressure or vacuum level. Suitable pressure sensors are known in the art and are commercially available from, for example, Honeywell Corporation (Morristown, N.J.). Examples include the Honeywell 26PC and 140PC series differential vacuum sensors and Sensym SDX pressure sensors.

Variable-Resistance Fluidic Resistors

In preferred embodiments, the vacuum-driven fluidics system of the present invention further includes a variable-resistance fluidic resistor in either the sample fluid path between the sample tube and the flow cell, in the sheath fluid path position between the sheath fluid reservoir and the flow cell, or both. Preferably, the variable-resistance fluidic resistor is incorporated into the sheath fluid path, as exemplified, below.

By varying the resistance of the variable-resistance fluidic resistor, the relative proportion of sheath fluid and sample fluid drawn through the flow cell can be modulated. As the total flow rate through the flow cell is held constant, modulation of the relative proportion of sheath fluid and sample fluid drawn through the flow cell also controls the sample fluid flow rate through the flow cell.

Preferably, the variable-resistance fluidic resistor is a viscously dominated restrictor, which facilitates balancing the pressures in the rest of the viscously dominated fluid circuit. In preferred embodiments, a viscously dominated restrictor is achieved by using a length of tubing or similar conduit having essentially a constant internal diameter. The resistive force, for a fluid of a given viscosity, depends on the length and internal cross-sectional area of the conduit, and the length is selected to provide the desired resistance. In contrast, simply pinching a tubing at a single point, or using a valve (such as a needle valve) to provide a flow restriction, results in a convective acceleration. Although this provides variable-resistance, it is less desirable in a viscously dominated system. Due to the effects of temperature on viscosity, the temperature dependence of the resistance of the sheath fluid line incorporating the viscously dominated fluidic resistor is the same as the temperature dependence of the resistance of the sample fluid line. Thus, the ratio of the sample fluid line and sheath fluid line resistances remains the same as the temperature is varied. In contrast, as pinching is convectively dominated and the resistance is not a function of temperature, the use of a pinching-type resistance would result in a change in the ratio of the path resistances with a change in temperature.

Typically, the conduit consists of a length of a glass, plastic, or steel tubing. Suitable tubing is available commercially in a variety of diameters. Typically, the diameter will be selected such that the desired flow resistance can be achieved with a convenient length of tubing, and then minor adjustments to the flow resistance will be made by modifying the length of the tubing. The diameter and length of the tubing will be selected based on the application, following the guidance herein.

A variable-resistance fluidic resistor may provide a choice between a plurality of discrete resistance settings. Alternatively, a variable-resistance fluidic resistor may provide a continuously adjustable resistance. Examples of different variable-resistance fluidic resistors are described below and in the figures.

Variable-resistance fluidic resistors that provide alternative discrete levels of fluidic resistance preferably are implemented by providing multiple, valve-selectable, parallel fluidic channels, each providing a distinct fluidic resistance. Alternative total fluidic resistance levels of the variable-resistance fluidic resistor, as a whole, are achieved by selecting which of the alternative internal fluidic channels are available for flow through the variable-resistance fluidic resistor.

Variable-resistance fluidic resistor that provide a continuously variable resistance are preferably implemented by providing a length of at least partially compressible or deformable material, such as length of plastic tubing, and a means for applying an adjustable pressure to the outside of the tubing. The tubing is selected such that the uncompressed tubing provides the lowest level of resistance desired. An increase in the pressure applied to the outside of the tubing will change alters the diameter and/or shape of the tubing, thereby increasing the fluidic resistance.

Description Based on the Figures

FIG. 1

FIG. 1 depicts a schematic representation of elements of a typical flow cytometer useful with the fluidic system of the present invention. Flow cell 100 includes flow cell chamber 106, sample inlet port 108, and a sheath inlet port 110. The sample inlet port 108 and sheath inlet port 110 are adapted to provide particle-containing fluid sample and particle-free sheath fluid, respectively, into the flow cell chamber 106. Flow cell chamber 106 converges to an opening that is joined to cuvette channel 104, which passes through cuvette 102.

In use, sample fluid containing the particles to be analyzed is introduced into the flow cell 100 through sample inlet port 108, and particle-free sheath fluid is introduced into the flow cell through sheath inlet port 110. Fluids exit through cuvette channel 104 and are directed to a waste receptacle (not shown). The flow cell is designed such that the sheath fluid forms an annular flow coaxial with the sample fluid, thereby creating a hydrodynamically focused flow of particle-containing sample fluid in the center of the fluid stream, surrounded by particle-free sheath fluid, as the fluid convectively accelerates through the converging path of the flow cell. The combined fluid stream consisting of sheath fluid and sample fluid is referred to herein as the "sample stream", "flow stream" or "particle stream".

Optical analysis of the particles within the sample stream is carried out by exposing the sample stream in detection region 120 to excitation light from one or more excitation light sources and detecting light emanating from the detection region 120 using one or more photodetectors (not shown). Cuvette 102 is constructed, at least in part, from an optically clear material to enable optical excitation and detection. FIG. 1 depicts the use of two excitation light sources. Excitation light source 118 emits a first beam of light that is focused by lens 116 onto the sample stream at a first interrogation point within detection region 120. Excitation light source 119 emits a second beam of light that is focused by lens 116 onto the sample stream at a second interrogation point within detection region 120, wherein the second interrogation point is downstream of the first interrogation point by a distance 122. A mirror or beam-splitter 117 is used to redirect the second beam to be essentially parallel the first beam at the interrogation points.

Typically, for each of the multiple excitation light sources, multiple detectors (not shown) are present to detect fluorescent light emitted from particles in the sample stream, each detector configured to detect emitted light within a defined range of wavelengths. In addition, additional detectors are positioned to detect excitation light from at least one excitation light source that is scattered by particles at a low angle relative to the excitation beam, referred to as forward scatter light, and excitation light that is scattered by particles at nearly right angles to the excitation beam, referred to as side scatter light. Suitable photodetectors for use in a flow-type particle analyzer include, for example, photomultiplier tubes (PMTs), avalanche photo diodes, photodiodes, or any other suitable light-detecting device.

The spatial separation of the interrogation points allows for the particles to be exposed to each of the excitation lights, which are of distinct wavelengths, separately. As the particles move through the cuvette channel 104, they are first exposed to the excitation light from excitation light source 118 at the first interrogation point. The particles then move out of the first interrogation point and into the second interrogation point where they are exposed to the excitation light from excitation light source 119. The time it takes for a particle to move from the first interrogation point to the second interrogation point is referred to herein as the "laser delay".

The laser delay is an important parameter that is used to electronically match up signals obtained from the emissions of a particle exposed to the first excitation late with signals from the emissions of the same particle exposed to the second excitation light, so that that the signals are all identified as originating from the same particle. The laser delay, for a given distance 122 between interrogation points, depends entirely on the flow rate through the cuvette channel 104. For at least this reason, the flow rate through the flow cell should be maintained constant during the analysis of sample particles.

The flow rate through the flow cell can be measured by analyzing a sample of test particles that are detectable at each interrogation point. For each particle, the time between the signals obtained from the emissions of the particle exposed to the first excitation light and the signals from the emissions of the particle exposed to the second excitation light is measured. As the distance 122 between interrogation points is known from the design of the instrument, the time delay between the first and second signals enables calculation of the flow rate through the detection region 120. Alternatively, the flow rate can be measured by measuring the accumulation of fluid downstream of the flow cell over a specified period of time.

FIG. 2

Figure 2:
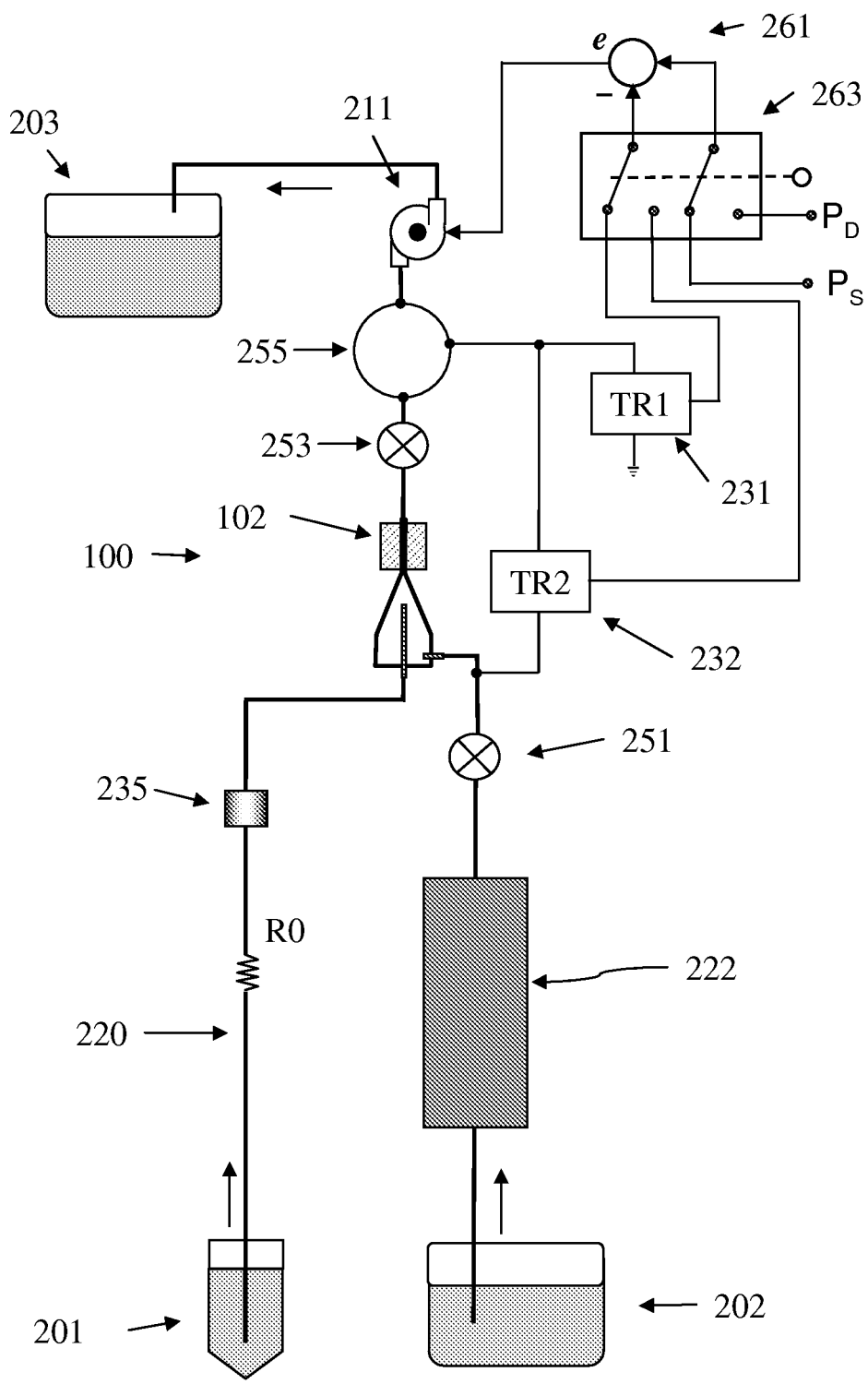
FIG. 2 provides a schematic representation of a vacuum-driven fluidic system of the present invention. The direction of fluid flow in FIG. 2 is from the bottom of the page towards the top, and flow cell 100 is shown in an orientation that is inverted relative its orientation in FIG. 1.

FIG. 2 depicts a schematic representation of elements of a fluidic system of the present invention. A system vacuum is developed by a vacuum pump 211, which draws sheath fluid from the sheath reservoir 202 and sample fluid containing the particles to be analyzed from the sample tube 201 through flow cell 100, wherein optical analysis is carried out (optics not shown). Waste effluent, which is the mixture of sample and sheath fluids exiting the flow cell, is discharged into waste reservoir 203.

Pulsations in the vacuum developed by vacuum pump 211, which typically is a diaphragm-type pump, are attenuated by accumulator 255, also referred to as a pulsation damper. The accumulator can be a sealed canister with an internal volume many times (e.g., 10 to 1000 times) the stroke volume of the vacuum pump.

Transducer 231 measures the pressure drop developed by vacuum pump 211 relative to atmospheric pressure. This pressure drop is referred to herein as the "static pressure drop". The static pressure drop preferably is measured from the interior of accumulator 255 so that a stable measurement is obtained.

Transducer 231 typically is connected to accumulator 255 by a short tube, such that the pressure in the tube equals the pressure in the accumulator. It is desirable to include an air bleed (e.g., a small orifice connecting the interior of the tube to the outside air) in the tube connecting transducer 231 and accumulator 255, positioned near the transducer, to allow a small amount of air to be drawn into and through the tube, drawn by the vacuum in the accumulator. The air bleed should be small enough such that the flow of air through the tube has an insignificant effect on the measurement of the static pressure drop. The minor air flow through the tube in the direction from the orifice (near the transducer) towards the accumulator prevents any fluid or foam that may be present in the accumulator from entering the tube to the transducer, which could affect the accuracy of the measurement.

Transducer 232 measures the pressure drop across the cuvette 102 (measured from upstream of the flow cell to the accumulator 255). This pressure drop is referred to herein as the "dynamic pressure drop". For a given total flow rate through the cuvette, the dynamic pressure drop is constant. Thus, by modulating the power of the vacuum pump 211 to provide a constant dynamic pressure drop, a constant total flow rate through the cuvette can be maintained.

Sample fluid is drawn through sample line 220 and into flow cell 100 through sample inlet port 108 (shown in FIG. 1). This entire sample path has a fluid resistance R0.

Sheath fluid is drawn through a variable-resistance fluidic resistor 222 and into flow cell 100 through sheath inlet port 110 (shown in FIG. 1). In a preferred embodiment, the fluidic resistance of the variable-resistance fluidic resistor is adjustable to multiple, discrete fluidic resistance settings. In another embodiment, the fluidic resistance of the variable-resistance fluidic resistor is continuously adjustable over a predefined range.

The relative proportions of sample fluid and sheath fluid that are drawn into flow cell 100 depend on the ratio of the sample line fluidic resistance R0 and the fluidic resistance of the variable-resistance fluidic resistor 222. Thus, by modulating the fluidic resistance of the fluidic resistance of the variable-resistance fluidic resistor 222, the ratio of sample fluid to sheath fluid can be controlled. If the total flow rate through the flow cell is held constant by maintaining a constant dynamic pressure drop, each reduction of the effective fluidic resistance of variable-resistance fluidic resistor 222 results in a decrease in the sample fluid flow rate and an increase in the sheath fluid flow rate. Thus, a desired sample flow rate can be selected by an appropriate modulation of the total fluidic resistance of the variable-resistance fluidic resistor 222, while maintaining a constant flow rate through the flow cell.

Valve 253 enables shutting off the fluid flow through the flow cell completely. The paused to allow, for example, a change to a new sample source after each sample analysis. In the present system, the flow of fluid may be paused by closing a valve situated in the fluid path between the flow cell and the pump. When this valve is closed, the dynamic pressure drop drops to zero, the first feedback loop, which is between the dynamic pressure drop and the pump, is stopped, and the second feedback loop, which is between the static pressure drop and the pump, is activated. The second feedback loop enables maintaining the static pressure drop at a constant level during the paused state, preferably maintaining the static pressure drop of the system that existed while in the running state prior to pausing the system (while under control of first feedback loop). When the flow of fluid through the flow cell is restarted, control of the pump is switched back to the first feedback loop, which enables maintaining a constant flow across the flow cell even after changes in the sample flow rate. This switching between feedback control circuits eliminates large fluctuations in the vacuum during transitions between running and paused states, while maintaining a constant flow rate through the flow cell for all samples.

Valve 251 enables shutting off the sheath fluid flow completely. Valve 251 is used to temporarily stop the sheath fluid flow and temporarily increase ("boost") the sample fluid flow rate following connection of the sample tube 201 to the sample line 220, in order to shorten the time it takes to draw sample fluid to the flow cell 100. When the sample fluid reaches the flow cell, valve 251 is opened, the flow of sheath fluid establishes a hydrodynamically focused stream, and the sample and sheath fluid flow rates return to the desired rates for analysis. Valves 251 and 253 preferably will be under automatic control in a coordinated manner, such that valve 253 can be opened for a predetermined time prior to opening valve 251 in order to permit a vacuum to be developed in said flow cell before opening said valve 251.

Controller 261 with switching mechanism 263 controls the switching between the modulation of the power of vacuum pump 211 to provide a constant dynamic pressure drop and modulation of the power of vacuum pump 211 to provide a constant static pressure drop. To maintain a constant dynamic pressure drop, the controller compares the dynamic pressure drop measured by transducer 232 to a stored desired dynamic pressure drop $P_D$. The desired dynamic pressure drop $P_D$ is determined during instrument setup as the dynamic pressure drop that provides the desired flow rate through the flow cell. To maintain a constant static pressure drop, the controller compares the dynamic pressure drop measured by transducer 231 to a stored desired static pressure drop $P_S$. The desired static pressure drop $P_S$ is the measured static pressure drop that corresponds to the instrument running with the desired flow rate through the flow cell, which depends on the selected setting of the variable-resistance fluidic resistor. Multiple values for the desired static pressure drop $P_S$ may be stored, each corresponding to a predefined resistance setting of the variable-resistance fluidic resistor. Alternatively, the desired static pressure drop $P_S$ may be stored immediately before pausing the system, and the system restarted with the same resistance setting of the variable-resistance fluidic resistor that was in effect just prior to pausing the system.

Preferably, automatic control of the pressure drop feedback circuits (through controller 261) and of valves 251 and 253, will be provided in a coordinated manner.

Flow sensor 235 is positioned on sample line 220 to provide a direct measure of the sample fluid flow rate. Suitable high precision liquid flow sensors and liquid flow meters with measurement ranges down to nanoliters per minute are commercially available from, for example, Sensirion Inc. (Westlake Village, Calif.). Flow sensor 235 is optional, but facilitates setting up the flow system. During instrument setup (system calibration), the fluidic resistance of variable-resistance fluidic resistor 222 is adjusted to provide the desired ratio of sheath to sample fluid, and the flow sensor provides an independent measure of the resulting sample fluid flow rate. Alternatively, the flow rate of the sample fluid can be measured by other means, such as by analyzing a sample containing a known concentration of test particles. By measuring the rate of detection of the test particles, the flow rate in the sample line 220 can be inferred.

The adjustment of the fluidic resistance of variable-resistance fluidic resistor 222 during instrument calibration to obtain a desired sample fluid flow rate can be automated, as described, below, with reference to FIG. 6.

FIG. 3

Figure 3:
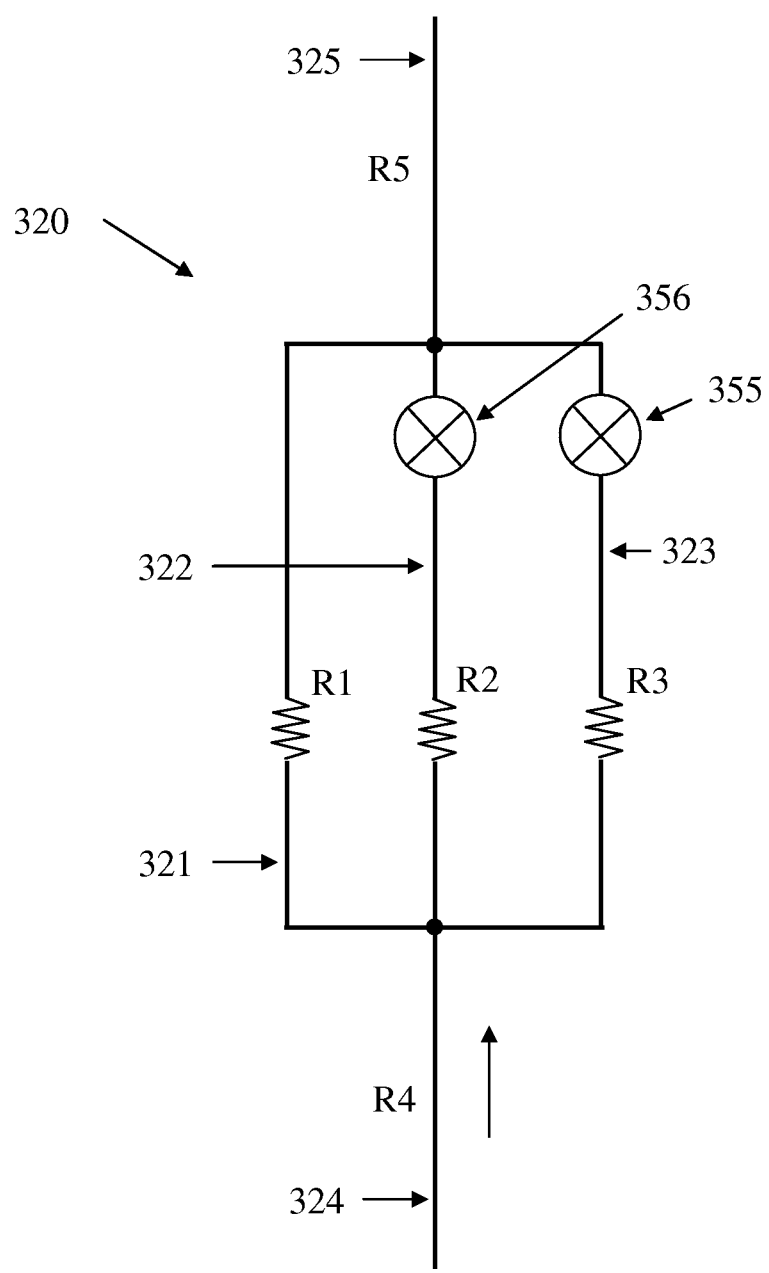
FIG. 3 provides a schematic representation of a variable-resistance fluidic resistor of the present invention. The variable-resistance fluidic resistor provides multiple, valve-selectable, discrete fluidic resistance levels.

FIG. 3 depicts a schematic representation of an embodiment of a variable-resistance fluidic resistor designed to provide alternative discrete levels of fluidic resistance. Within the variable-resistance fluidic resistor are multiple parallel fluidic channels, each providing a distinct fluidic resistance, and the alternative total fluidic resistance levels of the variable-resistance fluidic resistor, as a whole, are achieved by selecting which of the alternative internal fluidic channels are available for flow through the variable-resistance fluidic resistor.

Variable-resistance fluidic resistor 320 contains internal fluid channels 321, 322, and 323, which provide fluidic resistances R1, R2, and R2, respectively. The selection of which of the three parallel fluid channels are available for sheath fluid flow is controlled by two-way valve 355, which controls the flow through fluid channel 322, and two-way valve 356, which controls the flow through fluid channel 323. Fluid channel 321 is always open for sheath fluid flow. The maximum resistance of the variable-resistance fluidic resistor 320 is provided by flow through the single fluid channel 321, selected by closing both valves 356 and 355. Opening one or the other, or both, of the valves provides at least one fluid channel in parallel to fluid channel 321, which decreases the total fluidic resistance through the variable-resistance fluidic resistor 320.

Although variable-resistance fluidic resistor 320 contains three internal fluid channels, it will be clear that essentially any number of discrete levels of fluidic resistance can be achieved using a multiplicity of alternative parallel fluidic channels, each with a defined fluidic resistance, and valves to enable selection of the fluidic channels. In general, the equivalent resistance of a circuit having a set of N resistors in parallel is related to the resistance values of the constituent parallel channels as follows:

$$\frac{1}{R} = \sum_{i=1}^{N} \frac{1}{R_i},$$

wherein R is the equivalent resistance of a circuit, and each $R_i$ is the resistance of parallel channel I, and the summation is over all the N parallel channels.

The equivalent resistances of variable-resistance fluidic resistor 320 through the parallel circuit, from the point that internal fluid channels 321, 322, and 323 diverge until these internal fluid channels rejoin, for each of the option fluid paths defined by valves 356 and 355 are shown in the table, below.

Effective Resistance of Fluidic Resistor 320

| Valve 356 | Valve 355 | Total Resistance |
|---|---|---|
| closed | closed | R1 |
| open | closed | 1/(1/R1 + 1/R2) |
| closed | open | 1/(1/R1 + 1/R3) |
| open | open | 1/(1/R1 + 1/R2 + 1/R2) |

Each reduction of the effective fluidic resistance of variable-resistance fluidic resistor 320 results in an increase in the ratio of sheath to sample fluid flowing through the flow cell. If the total flow rate through the flow cell is held constant by maintaining a constant dynamic pressure drop, each reduction of the effective fluidic resistance of variable-resistance fluidic resistor 320 results in a decrease in the sample fluid flow rate. Thus, a desired sample flow rate can be selected by an appropriate modulation of the total fluidic resistance of the variable-resistance fluidic resistor, while maintaining a constant flow rate through the flow cell.

The total sheath fluid path from the sheath reservoir 202 to the flow cell 100 (shown in FIG. 2) includes sheath fluid line 324, having resistance R4, variable-resistance fluidic resistor 320, and sheath fluid line 325, having resistance R5. The total resistance of the sheath fluid path is the sum of the resistances of these three components, R4+R5+ the resistance of the variable-resistance fluidic resistor 320. Typically, the variable-resistance fluidic resistor 320 will provide the majority of the total resistance of the sheath fluid path.

FIG. 4

Figure 4A:
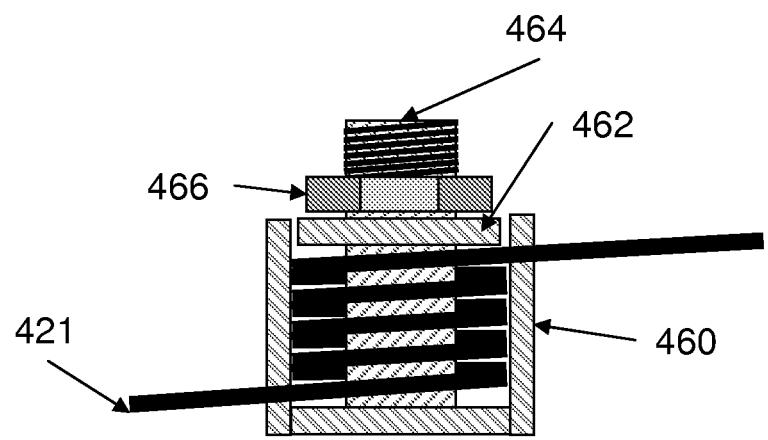
FIGS. 4a and 4b provide schematic representations of a continuously variable-resistance fluidic resistor of the present invention.
Figure 4B:
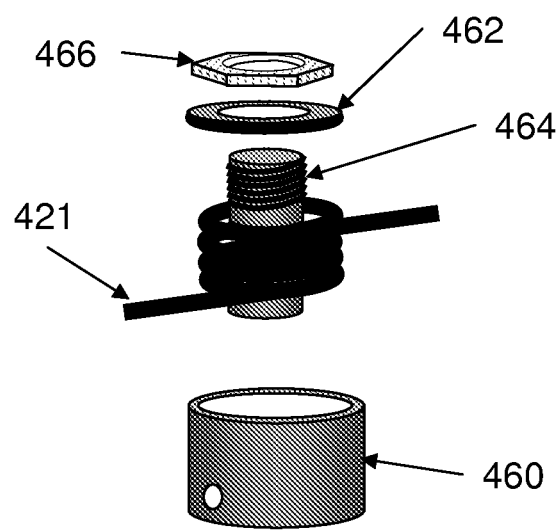

FIGS. 4a and 4b depict two views of a schematic representation of an alternative embodiment of a variable-resistance fluidic resistor wherein the resistance is continuously variable. In this embodiment, the modulation of the fluid resistance is achieved by compressing a length of tubing, thereby changing the inside diameter.

Sheath fluid line 421 is a compressible tubing, such as a peristaltic pump tubing. A section of the sheath fluid line 421 is coiled around center post 464 and positioned inside a cylindrical base housing 460. Holes in the base housing allow the tubing to enter and exit the base housing without being pinched. A circular top plate 464 is positioned inside the top opening of the base housing so as to form a cylindrical cavity containing the coil of sheath fluid line 421. Top plate 462 contains a whole that allows center post 464 to extends through top plate 462 such that the top plate can slide down into the base housing. The center post is threaded at the upper end, and a nut 466 is screwed onto the end of the center post. Tightening the nut presses top plate 462 onto the top of the coil of the sheath fluid line 421 compressing the sheath fluid line and increasing the fluidic resistance.

The fluidic resistance of sheath fluid line 421 is continuously variable, controlled by the force applied by the nut 466, and precise control over the change in resistance is possible. The tubing diameter and the number of windings in the coil will be selected to provide the range and control required for the particular application. The flow path of the sheath fluid is very simple, can be flushed easily for cleaning, and has no internal edges or other structures that might collect cells or particles.

It will be clear that the modulation of the fluidic resistance of the variable-resistance fluidic resistor can be automated to provide remote control of the fluidic resistance.

FIG. 5

Figure 5:
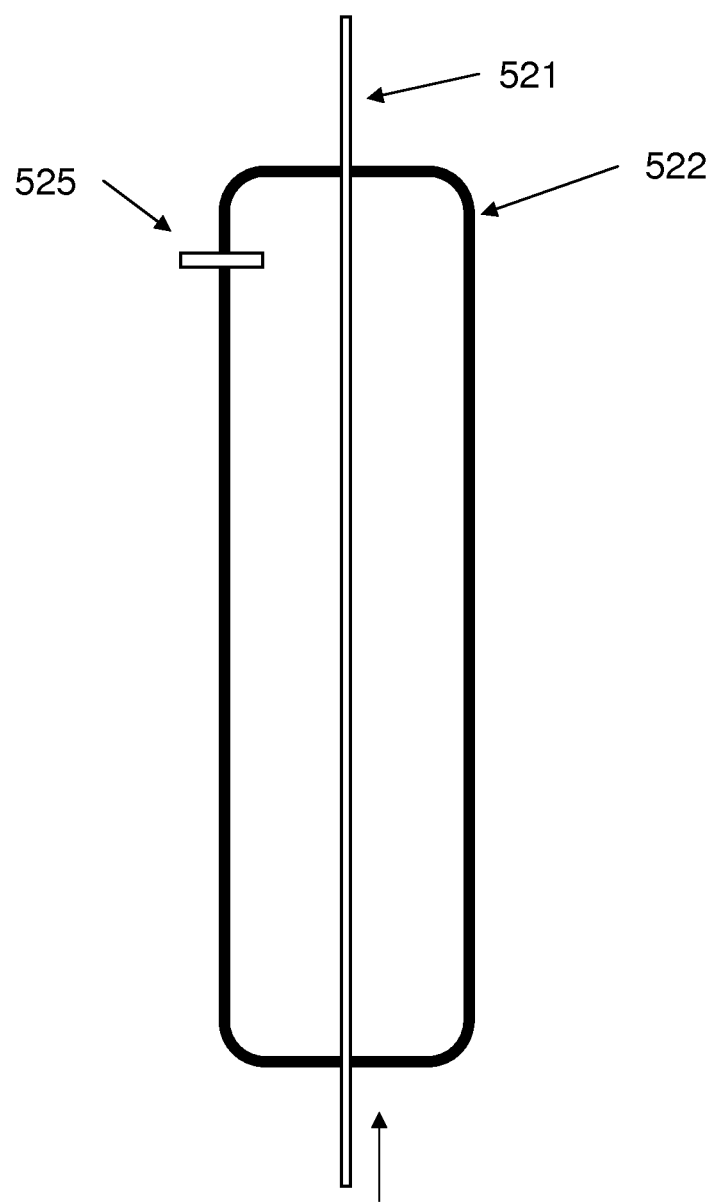
FIG. 5 provides a schematic representation of an alternative embodiment of the continuously variable-resistance fluidic resistor of the present invention.

FIG. 5 depicts a schematic representation of an alternative embodiment of a variable-resistance fluidic resistor wherein the resistance is continuously variable. Sheath fluid line 521 is a compressible tubing, such as a peristaltic pump tubing. The sheath line 521 is passed through a sealed pressurized tank 522, which is filled with a gas or fluid under pressure through inlet port 525. Changes in the pressure within the tank compress the sheath line, changing the fluidic resistance.

It will be clear that the modulation of the fluidic resistance of the variable-resistance fluidic resistor can be automated to provide remote control of the fluidic resistance.

FIG. 6

Figure 6:
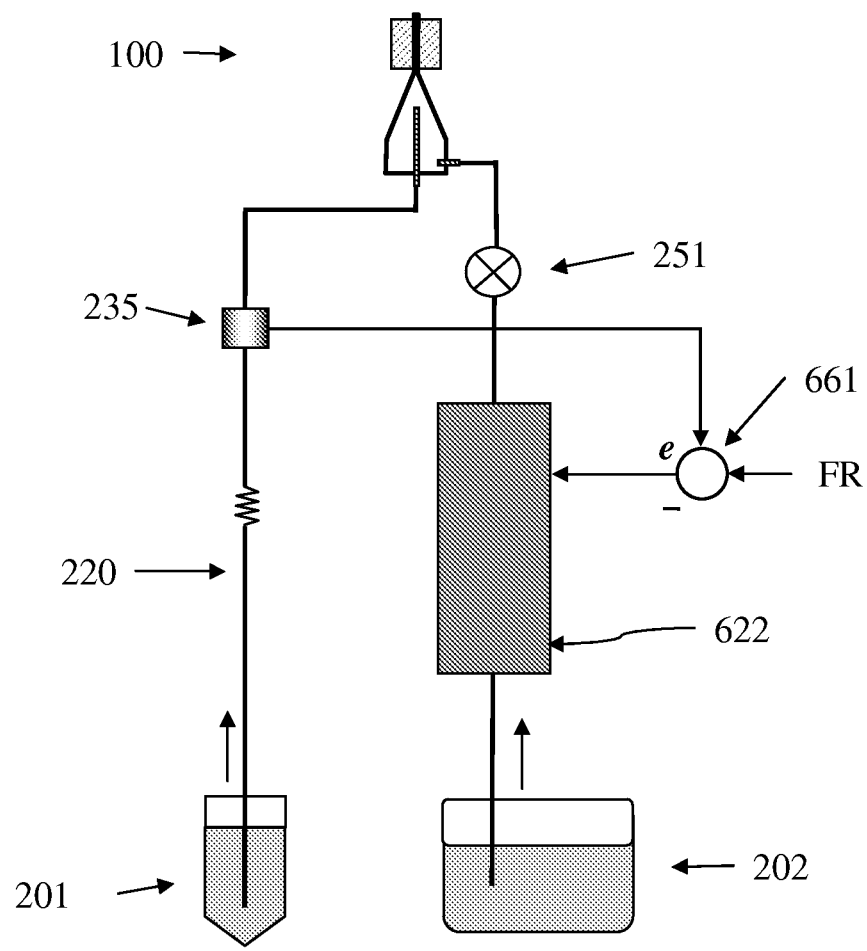
FIG. 6 provides a schematic representation of elements of an alternative embodiment of a vacuum-driven fluidic system of the present invention having a continuously variable-resistance fluidic resistor under the control of a feedback circuit that modulates the resistance in response to the sample fluid flow rate, as measured by a flow meter in the sample fluid line.

FIG. 6 depicts an automated feedback control circuit for automatically modulating the sample fluid flow rate to obtain a preselected sample fluid flow rate during system calibration. Continuously variable variable-resistance fluidic resistor 622 is configured to enable modulation of the fluidic resistance using a servomechanism. Examples of suitable variable-resistance fluidic resistors are as depicted in FIG. 4, wherein nut 466 is adjusted using a servomotor, or as depicted in FIG. 5, wherein modulation of the pressure source is under servomotor control. Controller 661 compares the flow rate measured by flow sensor 235 to a stored desired flow rate FR and modulates the fluidic resistance of variable-resistance fluidic resistor 622 until the measured flow rate matches the desired flow rate FR.

System Calibration

In general, the initial calibration of a flow-type particle analyzer containing the vacuum-driven fluidics of the present invention preferably is carried out using the following steps:

A. The resistance of the variable fluidic resistor is set to any convenient setting. Because the dynamic pressure drop required to maintain the desired flow rate through the flow cell is not dependent on the resistance of the continuously variable fluidic resistor, the resistance setting used as this step is not critical.

B. The dynamic pressure drop that will obtain the desired flow rate through the flow cell is determined. The value of the dynamic pressure drop is stored and used in the feedback control system to maintain a constant dynamic pressure drop.

C. The variable-resistance fluidic resistor is adjusted to give a desired sample flow rate, while maintaining the dynamic pressure drop. The sample flow rate preferably is measured by flow-rate meter in-line with the sample fluid line, as described above. In embodiments using a discrete value variable-resistance fluidic resistor, adjustments are made in step (C) to each of the discrete resistance levels to obtain each of the desired sample flow rates. Preferably, the static pressure drop corresponding to each of the sample flow rates is recorded, for use in pausing and restarting the system.

For example, using a discrete-value, variable-resistance fluidic resistor as depicted in FIG. 3, the variable fluidic resistor initially is configured with nominally long lengths of tubing for the internal fluid channels 321, 322, and 323. The adjustments in step (C) are carried out with valves 356 and 355 initially closed, such that sheath fluid travels only through fluid channel 321. This provides the highest level of resistance to the sheath fluid, which corresponds to the highest ratio of sample to sheath fluid and, the highest sample fluid flow rate. Fluid channel 321 is adjusted by, for example, changing the length of the tubing to obtain the desired "high" sample flow rate, while maintaining the dynamic pressure drop. Next, valve 356 is opened such that sheath fluid travels in parallel through fluid channels 321 and 322. This provides a reduced level of resistance to the sheath fluid, which corresponds to reduced sample fluid flow rate. Fluid channel 322 is adjusted to give the desired "medium" sample flow rate, while maintaining the dynamic pressure drop. Next, valve 355 is opened such that sheath fluid travels in parallel through fluid channels 321, 322, and 323. This provides a further reduced level of resistance to the sheath fluid, which corresponds to further reduced sample fluid flow rate. Fluid channel 323 is adjusted to give a desired "low" sample flow rate, while maintaining the dynamic pressure drop. It will be clear that although the setup described above describes the setting of three discrete fluidic resistance levels, the presence of two valves allows for up to four discrete fluidic resistance levels.

In embodiments using a continuously variable variable-resistance fluidic resistor, the resistance level is modulated, while maintaining the dynamic pressure drop, until the desired sample flow rate is obtained, preferably under automated control. For example, using a continuously discrete-value, variable-resistance fluidic resistor and control feedback circuit as depicted in FIG. 6, the resistance is modulated automatically in response to the measured sample flow rate until the desired flow rate is obtained.

Pausing and Restarting the System

One aspect of the present invention is an improved method for pausing a vacuum-driven fluidic system in a flow-type fluid analyzer that facilitates maintaining a constant vacuum pump power level when switching between running and paused states. Flow of fluid through the flow cell can be stopped (i.e., the system paused) by closing valve 253. In order to avoid fluctuations in the vacuum drawn by pump 211, control of the vacuum pump is switched, preferably automatically, to the static pressure feedback loop to maintain the static pressure drop at the constant value that existed immediately prior to pausing the flow. The vacuum pump power level required to maintain the desired dynamic pressure drop while the system is running should equal the power level required to maintain the corresponding static pressure drop (measure just prior to pausing the system) once the system is paused. The static pressure drop just prior to pausing the flow is determined either at the time of instrument calibration, as described above, or by measuring the static pressure drop prior to closing valve 253.

To restart the system, valve 253 is opened, allowing vacuum pump 211 to draw a vacuum through the flow cell. Control of the vacuum pump is switched, preferably automatically, to the dynamic pressure feedback loop, and the power to the pump is adjusted to maintain the dynamic pressure drop at the value determined at setup to provide the desired flow rate through the flow cell.

The system will routinely be paused to allow for replacement of the sample tube. Upon restarting, sample fluid from the new sample tube will need to be drawn through the sample fluid line before reaching the flow cell. It is desirable to speed up (boost) this initial flow of sample until the sample fluid line is full of sample fluid from the new tube. Maximum sample fluid flow is achieved by shutting off sheath fluid flow by closing valve 251. When restarting the system, valve 253 is opened for a predetermined time, which will be based on the flow rate and volume of the sample fluid line, prior to opening valve 251 in order to permit a vacuum to be developed in the flow cell before opening valve 251, thereby pulling sample fluid through the sample line and into the flow cell prior to opening valve 251.

We claim:

1. A method for maintaining a constant flow rate through a flow cell, the method comprising:
flowing a sample fluid through a sample fluid inlet port into a cuvette;
flowing a sheath fluid through a sheath fluid inlet port into the cuvette;
wherein the cuvette contains a cuvette channel having an input end and an output end, wherein the input end is in fluidic communication with the sample inlet port and the sheath fluid inlet port, and the output end is in fluidic communication with an outlet port and wherein the flowing comprises utilizing a vacuum pump having a controllable power level in vacuum communication with the outlet line and configured to draw a vacuum in the outlet line, thereby pulling the sample and sheath fluids through the cuvette;
measuring a dynamic drop pressure wherein measuring the dynamic drop pressure drop pressure comprises a utilizing first sensor configured to measure the dynamic pressure drop from the sheath fluid inlet port to said cuvette outlet port;
measuring static drop pressure wherein measuring the static pressure drop pressure comprises utilizing a second sensor configured to measure the pressure drop from said cuvette outlet port to atmospheric pressure; and
regulating the power of the vacuum pump in response to the dynamic pressure drop.

2. The method of claim 1, further comprising regulating the power of said vacuum pump in response to the static pressure drop.

3. The method of claim 1, further comprising adjusting the flow rate of the sheath fluid with a variable resistance fluidic resistor.

4. The method of claim 3, wherein the variable resistance fluidic resistor comprises a plurality of selectable fluidic paths.

5. The method of claim 3 where the variable resistance fluidic resistor is configured to provide continuously variable fluidic resistance.

6. The method of claim 5, wherein the variable resistor fluidic resistor is comprised of an at least partially compressible or deformable material and a controllable means for applying pressure on the outside of the conduit.

7. A method for maintaining a constant flow rate through a flow cell, the method comprising:

flowing a sample fluid through a sample fluid inlet port into a cuvette at a first flow resistance;

flowing a sheath fluid through a sheath fluid inlet port into the cuvette at a second flow resistance;

wherein the first or second resistance is continuously variable;

wherein the cuvette contains a cuvette channel having a input end and an output end, wherein the input end is in fluidic communication with the sample inlet port and the sheath fluid inlet port, and the output end is in fluidic communication with an outlet port and wherein the flowing comprises utilizing a vacuum pump having a controllable power level in vacuum communication with the outlet line and configured to draw a vacuum in the outlet line, thereby pulling the sample and sheath fluids through the cuvette;

measuring a dynamic drop pressure wherein measuring the dynamic pressure drop pressure comprises a utilizing first sensor configured to measure the dynamic pressure drop from the sheath fluid inlet port to said cuvette outlet port; and regulating the power of the vacuum pump in response to the dynamic pressure drop.

8. The method of claim 7, wherein the continuously variable first or second resistance is maintained via a variable resistor fluidic resistor comprised of an at least partially compressible or deformable material and a controllable means for applying pressure on the outside of the conduit.

9. The method of claim 7, further comprising automatically modulating the first or second flow resistance to obtain a preselected fluid flow rate in response to a signal from the first sensor.

10. The method of claim 7, further comprising measuring a static drop pressure by utilizing a second sensor configured to measure the pressure drop from said cuvette outlet port to atmospheric pressure.

11. The method of claim 7, further comprising automatically modulating the first or second flow resistance to obtain a preselected fluid flow rate in response to a signal from the second sensor.

\* \* \* \* \*